(12) United States Patent
Roumagnac

(10) Patent No.: US 10,412,979 B2
(45) Date of Patent: Sep. 17, 2019

(54) SYSTEM FOR THE HEAT TREATMENT OF ARTICLES

(71) Applicant: STERIFLOW, Roanne (FR)

(72) Inventor: Jean-Patrick Roumagnac, Roanne (FR)

(73) Assignee: STERIFLOW, Roanne (FR)

( * ) Notice: Subject to any disclaimer, the term of this patent is extended or adjusted under 35 U.S.C. 154(b) by 124 days.

(21) Appl. No.: 15/102,512

(22) PCT Filed: Jan. 29, 2015

(86) PCT No.: PCT/IB2015/050677
§ 371 (c)(1),
(2) Date: Jun. 7, 2016

(87) PCT Pub. No.: WO2015/114556
PCT Pub. Date: Aug. 6, 2015

(65) Prior Publication Data
US 2016/0302454 A1    Oct. 20, 2016

(30) Foreign Application Priority Data

Jan. 29, 2014 (FR) .................................... 14 50712

(51) Int. Cl.
*F24C 15/32* (2006.01)
*A21B 1/26* (2006.01)
(Continued)

(52) U.S. Cl.
CPC .................................... *A23L 3/10* (2013.01);
*A21B 1/26* (2013.01); *A23L 3/04* (2013.01);
*A61L 2/07* (2013.01);
(Continued)

(58) Field of Classification Search
CPC .... A47J 2027/043; A47J 27/04; A47J 39/003; A21B 1/26; A21B 1/24; F24C 15/322
(Continued)

(56) References Cited

U.S. PATENT DOCUMENTS

| | | | | |
|---|---|---|---|---|
| 3,926,106 | A | * | 12/1975 | Deusing .................... A21B 1/28 |
| | | | | 126/21 A |
| 4,233,495 | A | * | 11/1980 | Scoville ................ A47J 39/003 |
| | | | | 126/21 A |

(Continued)

FOREIGN PATENT DOCUMENTS

| | | |
|---|---|---|
| EP | 0 138 688 A2 | 4/1985 |
| EP | 1 462 156 A1 | 9/2004 |

(Continued)

OTHER PUBLICATIONS

Written Opinion of the International Searching Authority dated Jun. 16, 2015, issued in corresponding International Application No. PCT/IB2015/050677, filed Jan. 29, 2015, 7 pages.

(Continued)

*Primary Examiner* — Reginald Alexander
(74) *Attorney, Agent, or Firm* — Christensen O'Connor Johnson Kindness PLLC

(57) ABSTRACT

A system for the heat treatment of industrial quantities of food or pharmaceutical articles. The system includes an oblong enclosure that is sealed and can be pressurized and having a median longitudinal axis and an inlet for the injection of a heat transfer fluid, an inlet door for the insertion of articles, a support for the articles, which support can be arranged along the median longitudinal axis, such that the articles are placed inside a central space in the enclosure, a defined lateral space being provided between the enclosure and the central space. The enclosure includes an agitation means for agitating the heat transfer fluid, which means is arranged laterally in relation to the central space, in the lateral space located between the enclosure and the central space, to allow the circulation of the heat transfer fluid in a longitudinal direction parallel to the median longitudinal axis.

10 Claims, 2 Drawing Sheets

(51) Int. Cl.
*A23L 3/10* (2006.01)
*A23L 3/04* (2006.01)
*A61L 2/07* (2006.01)

(52) U.S. Cl.
CPC ....... *F24C 15/322* (2013.01); *A61L 2202/122* (2013.01)

(58) Field of Classification Search
USPC .......................................... 99/476, 474, 475
See application file for complete search history.

(56) References Cited

U.S. PATENT DOCUMENTS

| | | | | |
|---|---|---|---|---|
| 4,420,679 | A * | 12/1983 | Howe ................... | F24C 15/325 126/21 A |
| 5,615,603 | A * | 4/1997 | Polin ........................ | A21B 1/26 126/21 A |
| 5,768,982 | A * | 6/1998 | Violi ..................... | F24C 15/327 126/20 |
| 6,658,995 | B1 * | 12/2003 | DeYoung ............... | A21C 13/00 165/267 |
| 6,923,111 | B2 * | 8/2005 | Kiefer ................... | A23B 7/144 62/239 |

FOREIGN PATENT DOCUMENTS

| | | |
|---|---|---|
| FR | 940 097 A | 12/1948 |
| FR | 1 465 121 A | 1/1967 |
| GB | 719 880 A | 12/1954 |

OTHER PUBLICATIONS

International Preliminary Report on Patentability dated Aug. 2, 2016, issued in corresponding International Application No. PCT/IB2015/050677, filed Jan. 29, 2015, 1 page.
International Search Report dated Jun. 16, 2015, issued in corresponding International Application No. PCT/IB2015/050677, filed Jan. 29, 2015, 7 pages.
Written Opinion dated Jun. 16, 2015, issued in corresponding International Application No. PCT/IB2015/050677, filed Jan. 29, 2015, 6 pages.

* cited by examiner

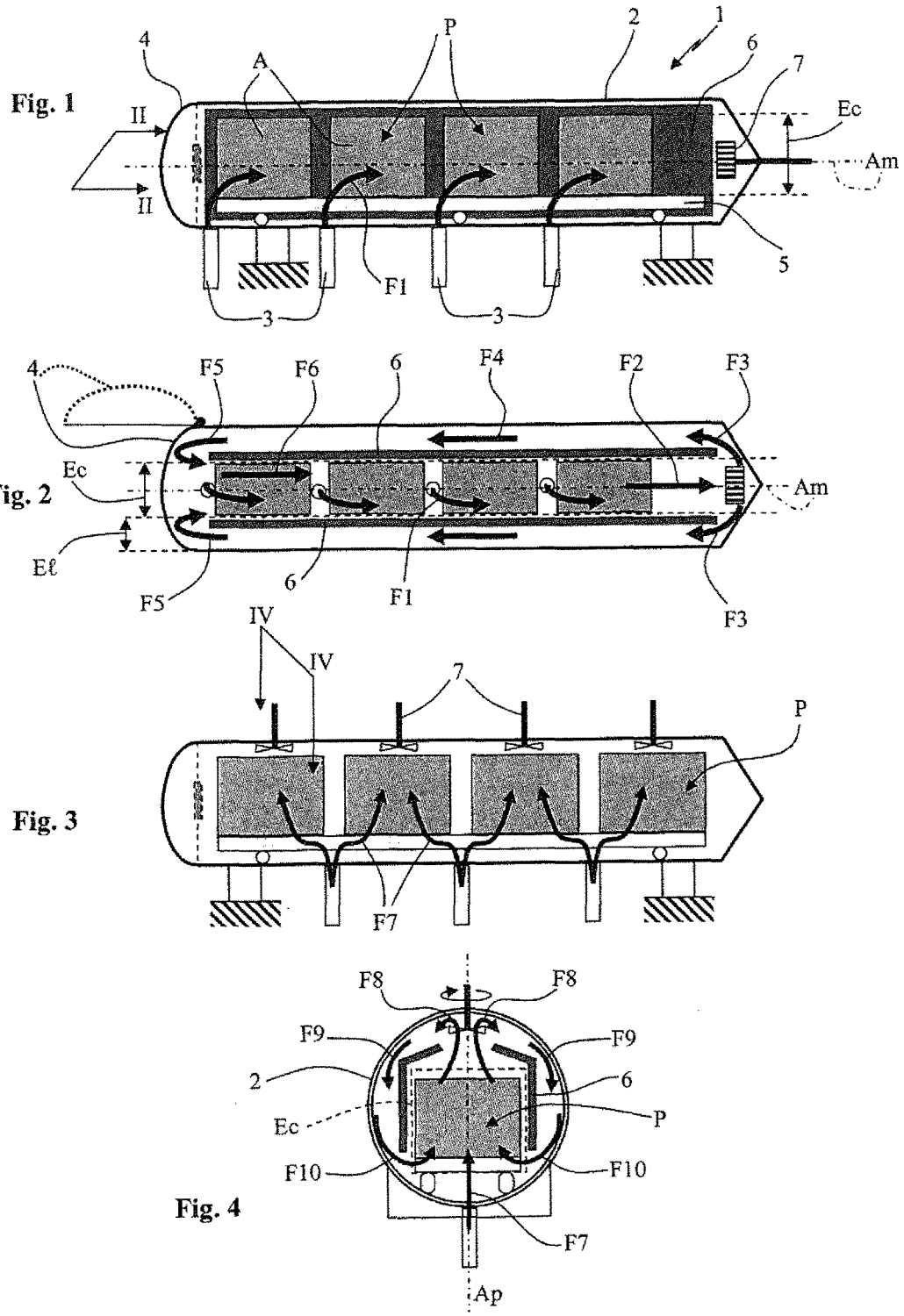

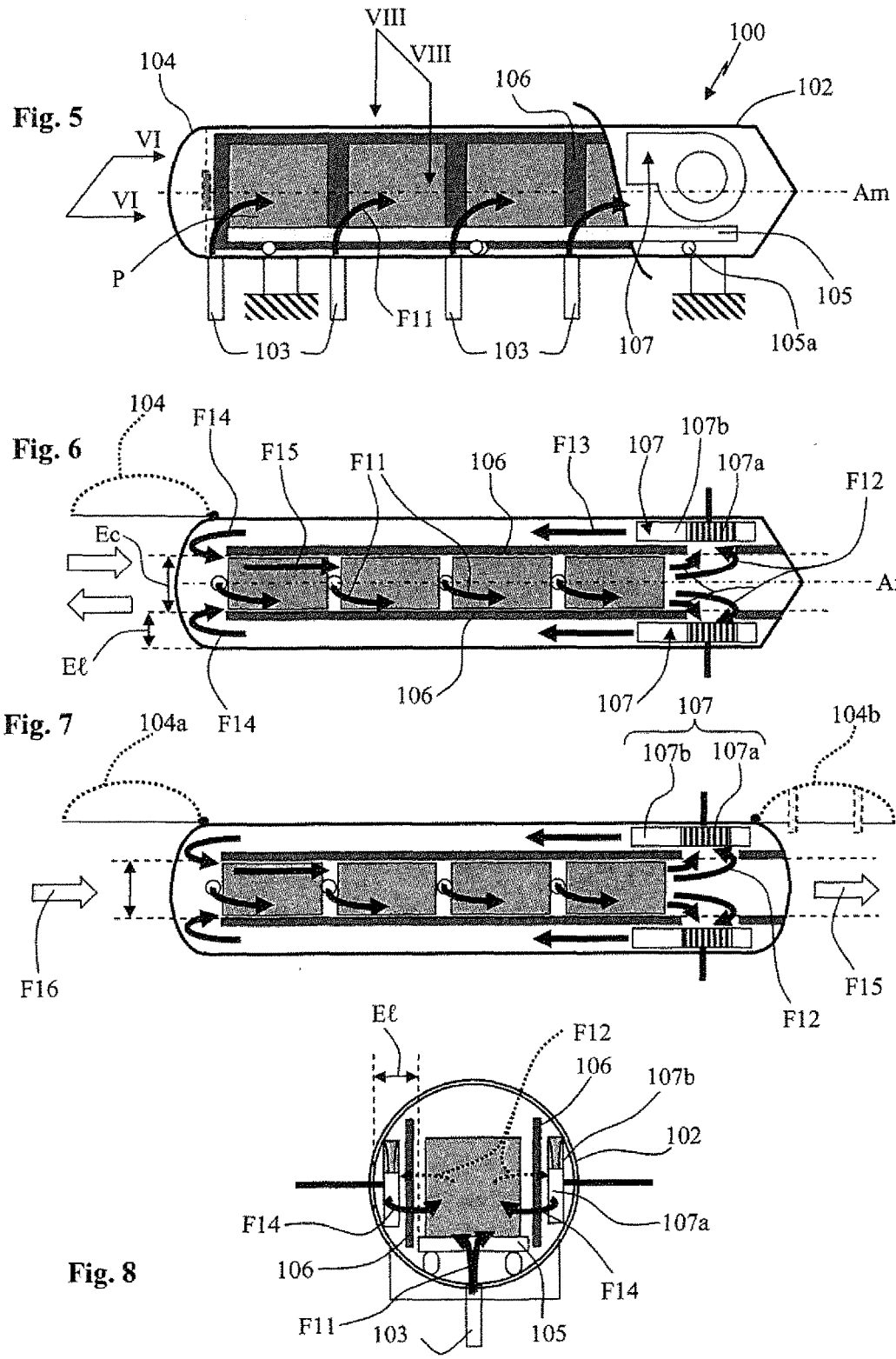

SYSTEM FOR THE HEAT TREATMENT OF ARTICLES

The invention relates to a system for the heat treatment of articles, in particular an autoclave or sterilizer.

Many food and pharmaceutical products must undergo a heat treatment (cooking, pasteurization, sterilization) in order to be sold. For example, this involves liquid products such as dairy products, soups, purées, fruit juices, as well as solid products contained in various packaging such as cans.

The heat treatment must be able to be done homogenously on an industrial quantity of articles. An industrial quantity refers to a weight exceeding 100 kg, and more specifically a weight of one ton or more, of articles.

Several systems are currently known. The present invention relates to horizontal autoclaves.

Such a known autoclave 1 is illustrated in FIGS. 1 and 2.

It comprises an oblong enclosure 2, cylindrical or parallelepiped, having a median longitudinal axis Am, the enclosure being sealed and able to be pressurized. This enclosure comprises:
at least one inlet 3 for the injection of the heat transfer fluid;
an inlet door 4 arranged a longitudinal end of the enclosure to allow the insertion of articles A in the enclosure; and
a support 5 for the articles, arranged along the median longitudinal axis, such that during use, the articles are placed centrally in the enclosure, in a central space Ec along the median longitudinal axis. A determined lateral space El is arranged between the enclosure and the articles.

The articles A to be treated are stored in baskets P, which are introduced in the autoclave through the door. The door is next closed and the heat treatment can begin.

Steam is commonly used as heat transfer fluid to heat the articles (cooking, pasteurization, sterilization), in particular food articles.

When it is used in pure form, i.e., without non-condensable gases (air), the heat transfer is effective and homogenous.

When it is mixed with air, which is systematically the case in an overpressure sterilizer currently used in the industry, the homogeneity of the mixture can only be ensured by effective mixing inside the enclosure.

This mixing makes it possible to ensure that there are no air pockets, and therefore cold zones, in which the articles (boxes, jars, bags, trays, etc.) would be under-sterilized. It also makes it possible to improve the exchange coefficient on the treated articles if the circulation speed around the articles is sufficient.

To improve the inner circulation of the heat transfer fluid, the enclosure 2 is equipped with an inner covering 6 made up of solid walls laterally separating the articles from the enclosure. In other words, the lateral space El arranged between the articles A and the enclosure 2 is defined by the enclosure 2 and the inner covering 6.

Different systems using this "air and steam mixing" method exist.

In a first type of sterilizer illustrated in FIGS. 1 and 2, a mixing means 7 is arranged axially on the median longitudinal axis Am of the horizontal sterilizer. The mixing means is either an axial fan or a centrifugal turbine (sterilizer from the STERISTEAM® brand by BARRIQUAND-STERIFLOW®).

However, experience has shown that this type of sterilizer is not satisfactory because the configuration limits, de facto, the size of the mixing means and therefore its effectiveness. Colder pockets may therefore still exist, such that it may prove necessary to extend the heat treatment and mixing duration.

Furthermore, with this type of sterilizer, the cooling phase of the product after the sterilization phase can be done using two different methods.

A first method consists of circulating water cooled by a heat exchanger in the enclosure. This method is very effective in terms of speed of cooling, but involves significant wetting of the products.

A second, so-called "dry" method consists of injecting air cooled by a cold battery into the enclosure. However, this injection of cold air causes the condensation of the steam present in the enclosure on the products, which wets them slightly.

It is therefore systematically necessary to allow the product to rest after sterilization so as to allow the water to evaporate, which extends the overall treatment time. The mixing means traditionally used, due to its necessarily reduced dimensions, cannot be used to accelerate the cooling phase.

One aim of the present invention is to shorten the treatment duration, in particular by shortening the duration of the cooling phase. The interest of a higher circulation speed is crucial.

In order to try to resolve the problems posed by this type of sterilizer, a second type of sterilizer has been proposed, illustrated in FIGS. 3 and 4, wherein the mixing means 7 is arranged radially so as to generate a radial circulation of the heat transfer fluid, basket by basket. In so doing, it was necessary to provide at least as many mixing means 7 as there are baskets P to be sterilized.

However, although the size of each mixing means is smaller than in the first type of sterilizer, the number is multiplied, which increases the cost and complexity of the equipment (maintenance of the motors, maintenance of the sealing systems of the driveshaft, etc.).

Furthermore, the radial systems require a more complicated inner covering for the creation of gas tunnels in each basket.

The aim of the present invention is therefore to propose a reliable system for the heat treatment of articles in an industrial quantity (from 100 kg up to 10 tons, or even more), allowing better heat treatment with an equal energy expenditure, that is more cost-effective while allowing a fast treatment rhythm.

To that end, the invention relates to a system for the heat treatment of articles comprising:
an oblong enclosure having a median longitudinal axis, the enclosure being sealed and able to be pressurized, and comprising:
  at least one injection inlet for a heat transfer fluid;
  an inlet door arranged at one longitudinal end of the enclosure to allow the insertion of the articles in the enclosure;
a support for the articles, able to be arranged along the median longitudinal axis, such that during use, the articles are placed inside a central space in the enclosure, along the median longitudinal axis, a determined lateral space being arranged between the enclosure and the central space;
wherein the enclosure comprises at least one means for mixing the heat transfer fluid arranged laterally relative to the central space, in the lateral space situated between the enclosure and the central space, to ensure the circulation of the heat transfer fluid in a longitudinal direction parallel to the median longitudinal axis.

According to other embodiments:

the system may further comprise at least one solid wall arranged longitudinally between the mixing means and the central space, such that during use, the heat transfer fluid mixed by the mixing means is channeled toward one end of the enclosure before returning back toward the articles;

the mixing means can be a centrifugal turbine;

the centrifugal turbine can be provided with an ejection volute for the heat transfer fluid mixed by the turbine during use;

the system may comprise two mixing means arranged laterally relative to the median longitudinal axis, in the lateral space situated between the enclosure and the central space, and on either side of the central space;

the support can be an apron mounted sliding relative to the enclosure;

the injection inlet for the injection of a heat transfer fluid is intended to inject an air/steam mixture;

the enclosure may further comprise an outlet door arranged at a second longitudinal end of the enclosure, opposite the inlet door relative to the central space;

the system can comprise at least one storage basket for the articles; and/or the system can comprise at least one discharge outlet for the heat transfer fluid.

Other features of the invention will be set out in the description provided below, done in reference to the appended figures, which respectively show:

FIG. 1, a diagrammatic sagittal sectional view of a first embodiment of a heat treatment system according to the state of the art;

FIG. 2, a diagrammatic cross-sectional view, from above, along line II-II, of the heat treatment system of FIG. 1;

FIG. 3, a diagrammatic sagittal sectional view of a second embodiment of a heat treatment system according to the state of the art;

FIG. 4, a diagrammatic front sectional view, along line IV-IV, of the heat treatment system of FIG. 3;

FIG. 5, a diagrammatic sagittal sectional view of a first embodiment of a heat treatment system according to the invention;

FIG. 6, a diagrammatic cross-sectional view, from above, along line VI-VI of the heat treatment system of FIG. 5;

FIG. 7, a diagrammatic cross-sectional view, from above, of a second embodiment of a heat treatment system according to the invention; and FIG. 8, a diagrammatic front sectional view, along line VIII-VIII, of the heat treatment system of FIG. 7.

Steam is commonly used as heat transfer fluid to heat the articles (cooking, pasteurization, sterilization), in particular food articles.

It is injected directly into the enclosure. Preferably, the enclosure 2 comprises several steam injection inlets 3, advantageously as many inlets as there are baskets P, or even several steam injection inlets per basket. The injection is then done via the side of each basket, laterally, from above and/or below.

Traditionally, these inlets are made up of secondary tubings of a main tubing running inside or outside the enclosure.

As shown by FIGS. 1 to 4, the general principle of the mixing, known by the sterilizers of the state of the art, consists of arranging a mixing means across from a heat transfer fluid inlet relative to the basket(s), i.e., relative to the central space Ec. It is then implemented such that it suctions the heat transfer fluid from the central space where the baskets P are located so as to favor the flow of heat transfer fluid from the injection inlet through the basket(s). In other words, the fluid is not pulsed toward the central space by the mixing means, but is suctioned outside the central space.

The flow of heat transfer fluid is then discharged by the mixing means 7 from the central space Ec where the baskets P are located, toward the lateral space E larranged between the inner covering and the enclosure. The heat transfer fluid is next suctioned in a loop.

The inventor has noted that several problems posed by the first type of sterilizer (FIGS. 1 and 2) are not resolved by radial mixing sterilizers (FIGS. 3 and 4) because they implement the same general operating principle according to which the mixing means, the heat transfer fluid inlet(s) and the baskets are all aligned relative to the central space Ec: in the first type sterilizer, they are arranged along the longitudinal median axis (see FIG. 2), and in the second sterilizer, they are arranged along an axis Ap perpendicular to the median longitudinal axis Am (see FIG. 4).

Yet it is traditionally considered that it is this alignment relative to the central space Ec that allows optimal mixing of the heat transfer fluid because the suction has a pressure loss, and is therefore maximal, between the heat transfer fluid inlet and the mixing means.

Thus, the circulation diagram of the air/steam mixture for the first type sterilizer described in the introduction is illustrated in FIGS. 1 and 2. The circulation is axial, i.e., parallel to the median longitudinal axis Am. After having been introduced into the central space Ec along the arrows F1 from the inlet(s) 3, the heat transfer fluid circulates in the central space Ec along the arrow F2, then is suctioned by the mixing means 7. The heat transfer fluid then diverges from the mixing means. The circulation of the heat transfer fluid from the mixing means is then done radially, toward the walls of the enclosure, along the arrows F3, then longitudinally in the lateral space arranged between the enclosure and the articles along the arrows F4. Next, at the opposite end of the enclosure, the fluid recirculates radially along the arrows F5 and converges toward the center of the enclosure, then longitudinally along the arrow F6 toward the mixing means, which re-suctions the fluid and places it back in circulation.

The circulation diagram of the air/steam mixture for the second type of sterilizer described in the introduction is illustrated in FIGS. 3 and 4. The circulation is radial, over the height of the horizontal sterilizer.

After having been introduced in the central space along the arrows F7 from the heat transfer fluid inlet(s), the latter circulates radially in the central space, then is suctioned by the mixing means. The heat transfer fluid then diverges from the mixing means along the arrows F8, then circulates along the walls of the enclosure into the lateral space arranged between the enclosure and the articles, among the arrows F9. Next, at the opposite end of the enclosure, the fluid converges along the arrows F10 toward the central space of the enclosure, then the mixing means, which re-suctions the fluid and places it back in circulation.

In light of the pressure losses caused by the change in direction and the length of the enclosure, the output of the mixing means is low in the first type of sterilizer. To ensure sufficient mixing, the mixing means would need to be oversized and would therefore be bulky. To be able to place such a mixing means (turbine or fan) in the enclosure, it would be necessary either to design longer sterilizers, with no increase in the working sterilization volume, or to reduce the number of baskets in the sterilizer to leave space for the mixing means.

The alternative illustrated in FIGS. 3 and 4 is not fully satisfactory, since although the length of the fluid circuit is shorter (only over the height of the sterilizer), it requires a complex inner covering.

Furthermore, as with the first type sterilizer, the pressure losses through the baskets vary depending on the loading plan of the articles (the compactness of the packaging, the types of baskets or plates that are stacked, their separation, parasitic circuits, etc.). Therefore, the larger the sterilizer is, the larger the mixing means must be and the more powerful the motor driving them must be. Aside from the costs created, technical limitations appear, as well as vibration problems incompatible with lasting sealing of the sterilizer.

Dimensional and technical limits are therefore required, such that it is not possible to design economically viable large sterilizers from the known solutions.

The inventor saw that by going against the prejudice regarding the alignment of the fluid inlets and the mixing means relative to the central zone, and placing the mixing means in the lateral space arranged between the central space and the enclosure, the mixing obtained could have a much better quality.

To that end, the invention proposes to place the mixing means (preferably a turbine) in the space arranged between the articles and the enclosure, so as to mix the heat transfer fluid and cause it to circulate in a longitudinal direction. This arrangement allows the use of volutes making it possible to concentrate, accelerate and steer the heat transfer fluid directly toward the end across from the mixing means, improving the circulation of the heat transfer fluid in the enclosure, and consequently, the homogeneity of the heat treatment of the articles.

One example embodiment of the invention is illustrated in FIG. 5.

The system 100 for the heat treatment of articles according to the invention [comprises] an oblong enclosure 102 having a median longitudinal axis Am, the enclosure being sealed and able to be pressurized. It comprises:
at least one inlet for the injection of a heat transfer fluid 103;
an inlet door 104 arranged at a longitudinal end of the enclosure 102 to allow the insertion of the articles in the enclosure; and
a support 105 arranged along the median longitudinal axis, such that during use, the articles are placed inside a central space Ec in the enclosure, along the median longitudinal axis, a lateral space El being arranged between the enclosure and the central space.

Preferably, the articles are placed in storage baskets P, and the enclosure comprises as many heat transfer fluid inlets 103 as there are baskets.

According to the invention, the system comprises at least one mixing means 107 for the heat transfer fluid arranged laterally relative to the central space Ec, in the lateral space El arranged between the enclosure and the central space, and oriented so as to mix and circulate the heat transfer fluid in a longitudinal direction along the lateral space.

On the contrary, in the state of the art, the mixing means is either placed in the central space (FIGS. 1 and 2), or placed laterally, but oriented such that the heat transfer fluid is mixed radially (FIGS. 3 and 4).

Advantageously, the enclosure further comprises at least one solid wall 106 arranged between the mixing means and the central space, such that during use, the heat transfer fluid mixed by the mixing means is channeled toward an end of the enclosure while circulating longitudinally before returning toward the articles. These solid walls are advantageously metal sheets thus making up two lateral gas tunnels through which the mixture circulates.

FIG. 6 illustrates two solid walls 106 positioned longitudinally or parallel to the axis Am. They are more particularly positioned on either side of the central space Ec or of the support 105.

Advantageously, the system comprises two mixing means arranged laterally relative to the central space, in the lateral space determined between the enclosure and the central space, and on either side of the support 105.

Thus, the circulation diagram of the air/steam mixture for the sterilizer according to the invention is described relative to FIG. 6.

After having been introduced into the central space Ec along the arrows F11 from the inlet(s) 103, the heat transfer fluid circulates in the central space Ec, then is suctioned by the mixing means 107 situated laterally. The heat transfer fluid then diverges before the mixing means along the arrows F12. In other words, the circulation of the heat transfer fluid before the mixing means is done radially, toward the walls of the enclosure, along the arrows F12, then, from the mixing means 107, longitudinally in the lateral space arranged between the enclosure and the central space Ec along the arrows F13. Next, at the opposite end of the enclosure, the fluid recirculates radially along the arrows F14 and converges toward the center of the enclosure, then longitudinally along the arrow F15 in the central space Ec. The mixing means next place it back in circulation until the end of the treatment.

In the rest of the description, the heat transfer fluid is an air/steam mixture, but other heat transfer fluids may be used inasmuch as they are able to be mixed by the mixing means.

The mixing means being situated in the lateral space, it is possible to implement more substantial fans in the same internal bulk of the sterilizer, or with an identical performance, to reduce their size.

In general, the mixing means makes it possible to suction the heat transfer fluid and expel it in the longitudinal direction inside the enclosure.

Alternatively or in combination, owing to the free room in the lateral spaces El, it is possible to provide the mixing means with a volute and/or covering, to channel the flow of air/steam mixture entering the mixing means and/or leaving the mixing means.

Preferably, each mixing means is a centrifugal turbine 107a, such as a blade action turbine. Indeed, such a turbine suctions the air/steam mixture through its center and expels it laterally. This type of turbine is therefore particularly well suited to the arrangement according to the invention, since there is no pressure loss upon expulsion from the turbine, unlike the arrangement of the state of the art.

However, installed as-is in the sterilizer, with only inner covering metal sheets 106 to channel the flow, the performance of the turbines is close to 50%.

In the known sterilizers, as illustrated in FIGS. 1 to 4, it is possible to use centrifugal turbines as mixing means. Nevertheless, it is impossible to provide these turbines with volutes due to the bulk of these volutes and the placement of the mixing means relative to the baskets (axial-central or radial arrangement).

Owing to the lateral placement of the turbines 107a, relative to the central space Ec, it is possible to equip the turbines with volutes 107b.

The embodiment illustrated in FIGS. 5 to 8 advantageously comprises two centrifugal turbines 107a each provided with a discharge volute 107b making it possible to accelerate and guide the air/steam mixture leaving the turbine. The overall performance obtained may reach 75%.

Therefore, at identical power relative to the sterilizers of the state of the art, the device makes it possible to significantly increase the flow rate, and therefore the mixing and the circulation speeds.

Preferably, a mixing means therefore comprises a central suction pavilion, a centrifugal reaction turbine (with suction) and a discharge volute.

Furthermore, the use of centrifugal turbines is particularly interesting because the driveshafts 107c are positioned perpendicular to the median longitudinal axis. Owing to the lateral placement, the turbines are as close as possible to the enclosure, such that the shaft lengths needed are smaller than the length necessary when the turbine is placed axially. Owing to these smaller shaft lengths, the system according to the invention undergoes significantly fewer vibrations.

Also thanks to the lateral placement of the mixing means 107 relative to the central space Ec, each mixing means 107 is positioned outside the location occupied by the series of baskets filled with articles.

Thus, as illustrated in FIG. 7, the technical solution according to the invention makes it possible to provide two doors 104a and 104b in the sterilizer, since the mixing means are no longer along the median longitudinal axis, which frees the passage of baskets.

Thus, owing to the invention, the enclosure may comprise an outlet door 104b arranged at a second longitudinal end of the enclosure 102, opposite the inlet door 104a relative to the central space Ec and the support 105.

The presence of the two opposite doors allows a fast sterilization rhythm: while the sterilized baskets leave through the outlet door 104b in the direction of the arrow F15, baskets to be sterilized enter through the inlet door 104a in the direction of the arrow F16.

On the contrary, with a sterilizer only comprising one door 104, the entry along the arrow F17 and the exit along the arrow F18 are done via the same door (see FIG. 6).

In order to facilitate the entry and exit of the baskets, the support 105 for the articles (or the baskets comprising the articles) is advantageously an apron mounted sliding relative to the enclosure 102. The sliding system can be skates or casters 105a.

When the heat treatment is complete, the enclosure is still under pressure from the heat transfer fluid. Before opening the door(s), the enclosure should be depressurized by discharging the heat transfer fluid. To that end, the enclosure preferably comprises at least one outlet (not shown) for discharging the heat transfer fluid.

The invention makes it possible to implement mixing flow rates (gas circulation) significantly higher than with the traditional solutions. It therefore makes it possible to improve the temperature homogeneity in the entire enclosure and to favor the heat transfer.

The invention claimed is:

1. A system for the heat treatment of articles, comprising:
an oblong enclosure having a median longitudinal axis, the enclosure being sealed and able to be pressurized, and comprising:
at least one injection inlet for a heat transfer fluid;
an inlet door arranged at one longitudinal end of the enclosure to allow the insertion of the articles in the enclosure;
a support for the articles, able to be arranged along the median longitudinal axis, such that during use, the articles are placed inside a central space in the enclosure, along the median longitudinal axis, a determined lateral space being arranged between the enclosure and the central space;
wherein the enclosure comprises at least one means for mixing the heat transfer fluid arranged laterally relative to the central space, in the lateral space situated between the enclosure and the central space, to ensure the circulation of the heat transfer fluid in a longitudinal direction parallel to the median longitudinal axis, wherein the at least one means for mixing is arranged across from the at least one injection inlet relative to the central space so that the mixing means suctions the heat transfer fluid from the central space where the articles are located so as to favor the flow of heat transfer fluid from the inlet through the articles, the heat transfer fluid being suctioned outside the central space.

2. The system according to claim 1, further comprising at least one solid wall arranged longitudinally between the mixing means and the central space, such that during use, the heat transfer fluid mixed by the mixing means is channeled toward one end of the enclosure before returning back toward the articles.

3. The system according to claim 1, wherein the mixing means is a centrifugal turbine.

4. The system according to claim 3, wherein the centrifugal turbine is provided with an ejection volute for the heat transfer fluid mixed by the turbine during use.

5. The system according to claim 1, comprising two mixing means arranged laterally relative to the median longitudinal axis, in the lateral space situated between the enclosure and the central space, and on either side of the central space.

6. The system according to claim 1, wherein the support is an apron mounted sliding relative to the enclosure.

7. The system according to claim 1, wherein said at least one injection inlet is intended to inject an air/steam mixture.

8. The system according to claim 1, wherein the enclosure further comprises an outlet door arranged at a second longitudinal end of the enclosure, opposite the inlet door relative to the central space.

9. The system according to claim 1, comprising at least one storage basket for the articles.

10. The system according to claim 1, comprising at least one discharge outlet for the heat transfer fluid.

* * * * *